(12) United States Patent
Martin

(10) Patent No.: US 8,376,909 B1
(45) Date of Patent: Feb. 19, 2013

(54) THERAPY EVALUATION MACHINE FOR MEASURING RANGE OF MOTION OF A WRIST, A HAND AND FINGERS

(76) Inventor: Romeo J. Martin, Denver, CO (US)

(*) Notice: Subject to any disclaimer, the term of this patent is extended or adjusted under 35 U.S.C. 154(b) by 0 days.

(21) Appl. No.: 13/373,465

(22) Filed: Nov. 14, 2011

(51) Int. Cl.
*A61B 5/117* (2006.01)
*A61B 5/103* (2006.01)
*A63B 71/00* (2006.01)

(52) U.S. Cl. .............................. 482/2; 600/587; 600/595

(58) Field of Classification Search .................. 600/587, 600/595; 601/40; 482/8, 9
See application file for complete search history.

(56) References Cited

U.S. PATENT DOCUMENTS

2010/0042023 A1* 2/2010 Park et al. ........................ 601/40

OTHER PUBLICATIONS

Kinetec Hand and Wrist CPM 8080, 2005.*

* cited by examiner

*Primary Examiner* — Brian Szmal
(74) *Attorney, Agent, or Firm* — Edwin H. Crabtree; Ramon L. Pizarro

(57) ABSTRACT

A therapy evaluation machine used for measuring range of motion during the rehabilitation of an injury to a patient's wrist, hand or fingers. The machine includes a horizontal machine base with first and second frame members. A torque bar is mounted on the frame members and adapted for gripping by the patient's healthy and injured hand. A range of motion scale is mounted on the torque bar for visually measuring range of motion in degrees by the healthy and injured hand or fingers and to measure progress as the injured hand or fingers begin to heal. Also, the machine includes a strain gauge mounted on the torque bar and connected to a computer with digital display. The strain gauge is used for originating resistance on the torque bar and measuring torque applied thereto.

9 Claims, 6 Drawing Sheets

THERAPY EVALUATION MACHINE FOR MEASURING RANGE OF MOTION OF A WRIST, A HAND AND FINGERS

BACKGROUND OF THE INVENTION (a) Field of the Invention

This invention relates to a therapy evaluation machine used for measuring range of motion for various joints in the human body, and more particularly, but not by way of limitation, to a therapy evaluation machine used in measuring range of motion during the rehabilitation of a wrist, a hand and a finger injury.

(b) Discussion of Prior Art

Heretofore, a physical therapist had no practical mechanical or electrical apparatus for accurately measuring the healing progress of a patient's wrist, hand or finger injury other than visually observing the physical appearance of the injury and the movement of the injured joint. The subject invention provides a unique and accurate practical way of measuring the healing process of a joint injury over a period of time.

SUMMARY OF THE INVENTION

In view of the foregoing, it is a primary objective of the subject invention to provide an accurate visual measurement, digital display and printed record of the torque movement of an injured joint, such as a wrist, a hand and a finger of a patient.

Another key object of the invention is the periodic measurements of the injured joint provide factual confirmation to the patient's employer and insurance company of the healing progress made during the rehabilitation of the injury and provide the opportunity to return to work when the injury is sufficiently healed.

The subject therapy evaluation machine for gripping by a patient's hand or fingers includes a horizontal machine base disposed on a mounting plate. The base includes upwardly extending, spaced apart, vertical frame members for suspending a horizontal, exercise torque bar having a handle sleeve disposed therearound for gripping by a both healthy and injured hand. One end of the torque bar is attached to a round finger grip for gripping by both healthy and injured fingers. The finger grip is disposed next to a 360 degree, range of motion scale for visually measuring range of motion in degrees by the hand or fingers. An opposite end of the torque bar is coupled on a first gear box shaft extending outwardly from one side of a gear box. A second gear box shaft extends outwardly from an opposite side of the gear box and is coupled to a strain gauge. The strain gauge is used for originating resistance, when turning the torque bar, and also to receive and measure torque applied to the twisting movement of the torque bar. The strain gauge is electrically connected to a computer with a digital display for measuring the torque applied to the torque bar and strain gauge.

These and other objects of the present invention will become apparent to those familiar with different types of range of motion devices and exercise machines used during the therapy of joint injuries when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the therapy evaluation machine as described herein, and in which.

DETAILED DESCRIPTION OF THE PREFERRED EMBODIMENTS

Figure 1:
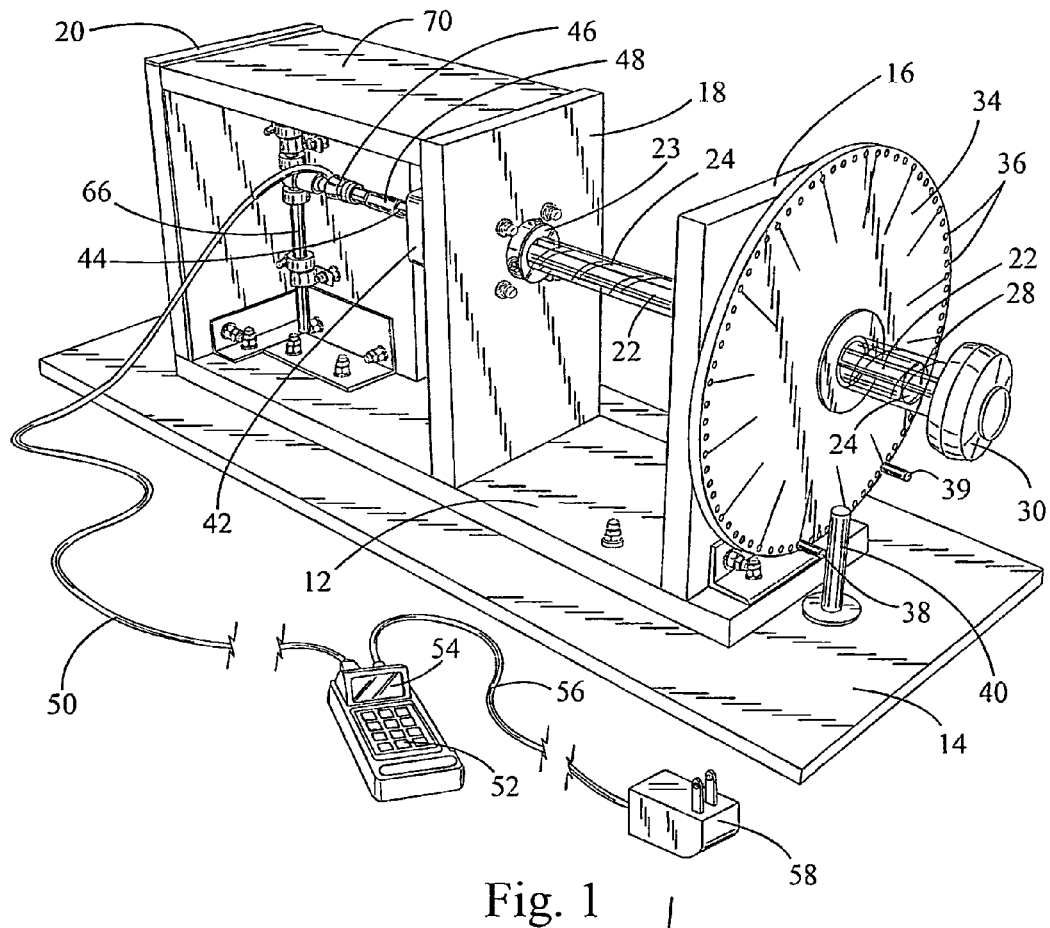
FIG. 1 is a perspective view of the subject therapy evaluation machine.
Figure 5:
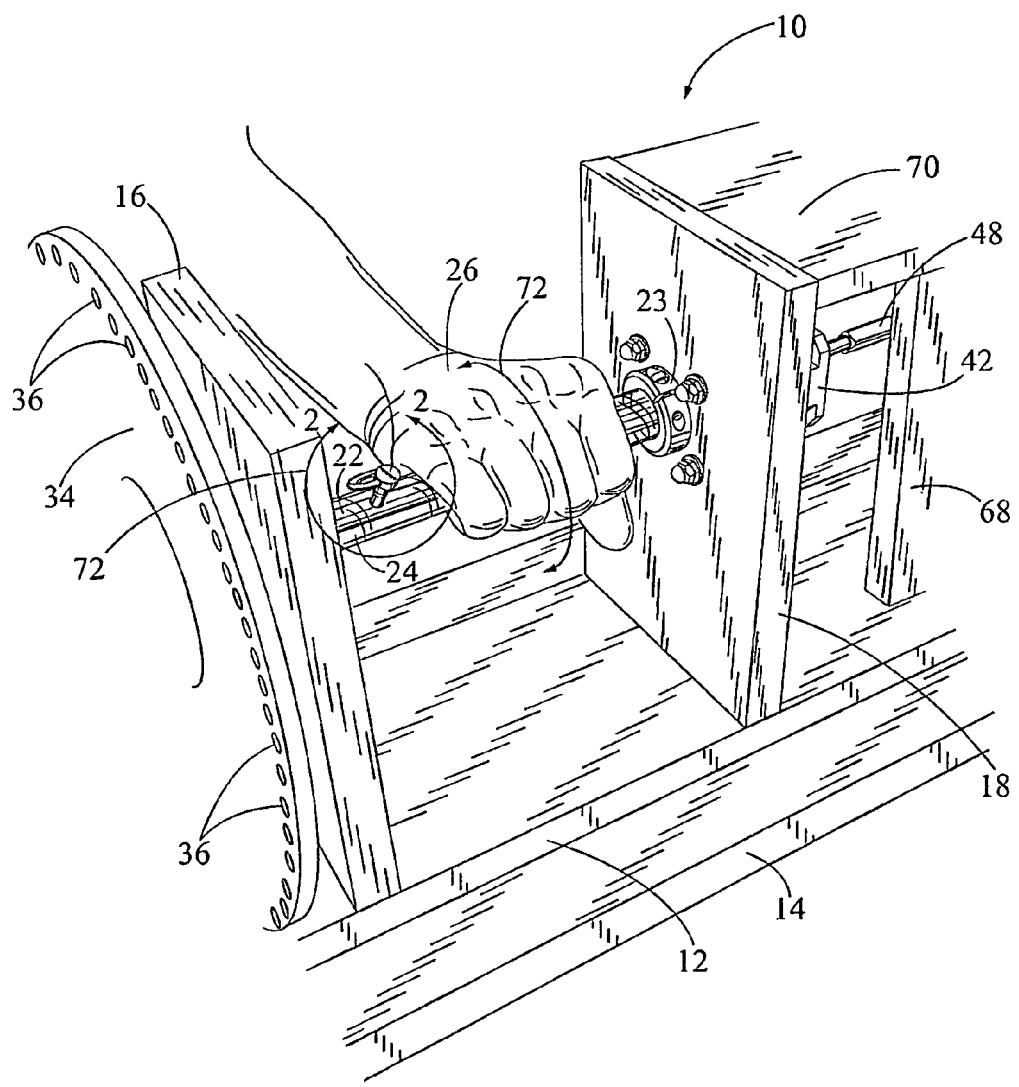
FIG. 5 is a perspective view of a human hand gripping the handle sleeve mounted on the torque bar.
Figure 6:
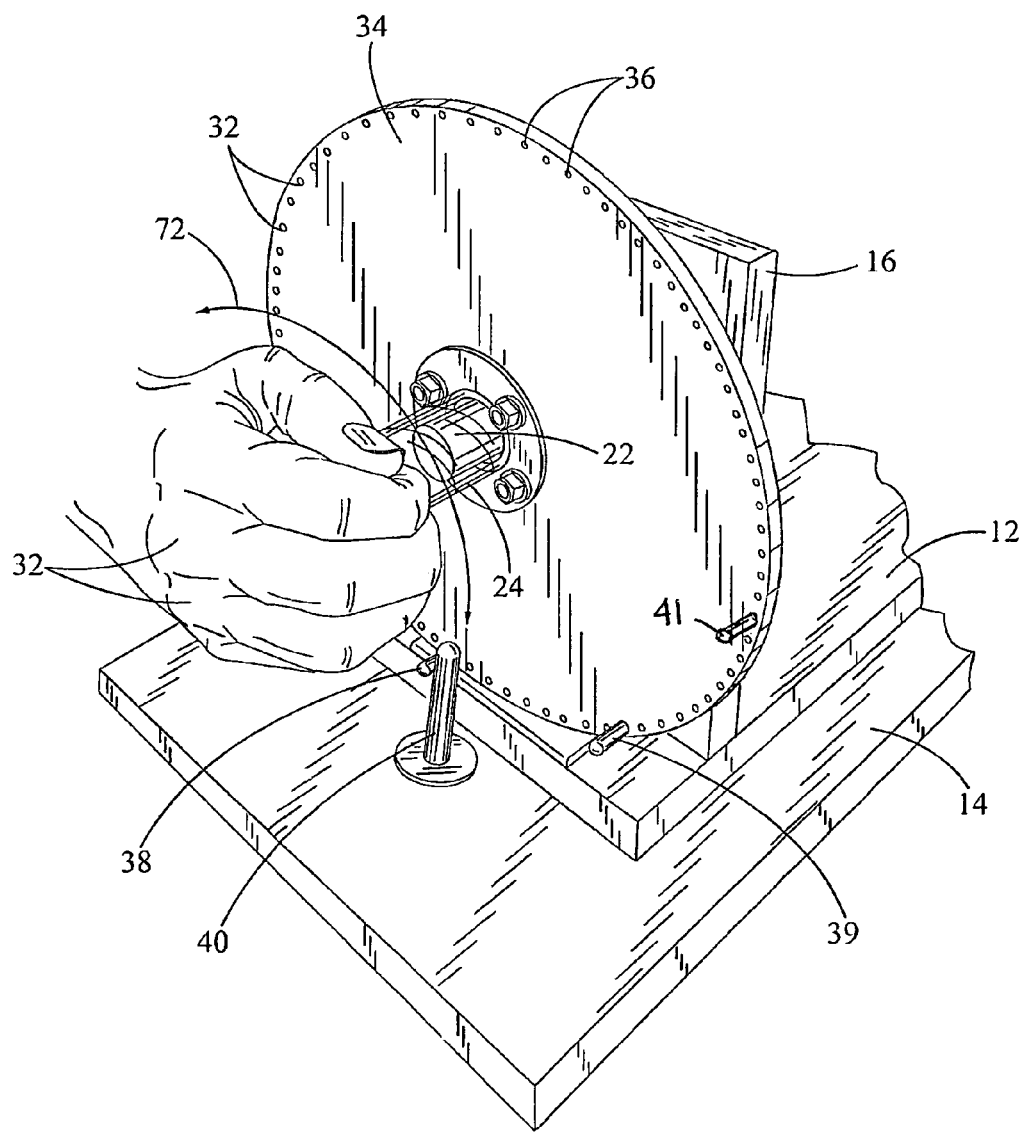
FIG. 6 is a perspective view of the fingers of a human hand gripping a finger grip mounted on an end of the torque bar.

In FIG. 1, a perspective view of the subject therapy evaluation machine is shown and having general reference numeral 10. The machine 10 includes a horizontal machine base 12 disposed on top of a mounting plate 14. The base 12 includes an upwardly extending, spaced apart, first frame member 16, a second frame member 18 and a third frame member 20. The first and second frame members 16 and 18 are used to suspend a horizontal, exercise torque bar 22 above the base 12. The bar 22 is mounted on the frame members 16 and 18 using bearings 23. Only one of the bearings 23 is shown in the drawings. The torque bar 22 includes a handle sleeve 24 disposed therearound for gripping by a either a healthy or an injured hand 26. The hand 26 is shown in FIG. 5. One end 28 of the torque bar 22 is attached to a round finger grip 30 for gripping by either healthy or injured fingers 32. The fingers 32 are shown in FIG. 6.

The finger grip 30 is disposed next to a 360 degree, range of motion scale 34 for visually measuring range of motion by the hand 26 or the fingers 32. The range of motion scale 34 is used for visually measuring the range of motion in degrees of the hand or fingers, which is compared to torque measurements from the torque bar 22 in inch pounds. The range of motion scale 34 includes spaced apart target holes 36 for receiving a pair of target pins 38 and 39. The target pin 38 is shown resting against an upwardly extending pointer 40 attached to the top of the mounting plate 14. In the drawing, the target pin 38 is set at zero degrees, while the other target pin 39 is set at 30 degrees on the scale 34.

In operation and during an initial meeting with a physical therapist, a patient, using the subject invention, will be asked to grip the torque bar 22 with a healthy hand and rotate the bar clockwise and move the scale 34 from the zero degree position to the 30 degree position, with the target pin 39 contacting the pointer 40. Then, the patient will be asked to grip the torque bar 22 with an injured hand. At this time, he or she may be able to only rotate the scale 34 from the zero degree position to a range of 10 to 15 degrees. This initial testing of the injured hand or fingers establishes a baseline or starting point for monitoring the improvement of the injury over a period of time when compared to the healthy hand or fingers.

An opposite end of the torque bar 22 is coupled on a first gear box shaft extending outwardly from one side of a gear box 42. The first gear box shaft isn't shown in the drawings. A second gear box shaft 44 extends outwardly from an opposite side of the gear box 42 and is attached to a strain gauge 46, using a coupling 48. The strain gauge 46 is configured to measure resistance to the rotating of the torque bar 22, and also to measure torque applied to the twisting movement of the torque bar 22. The strain gauge 46 is electrically connected, using electric lead 50, to a computer 52 with a digital display 54 for monitoring both the torque resistance sent and received as applied to the torque bar 22 and strain gauge 46. The computer 52 is shown with an electrical power lead 56 and a power outlet plug 58 for providing power to the computer 52 and the strain gauge 46.

Figure 2:
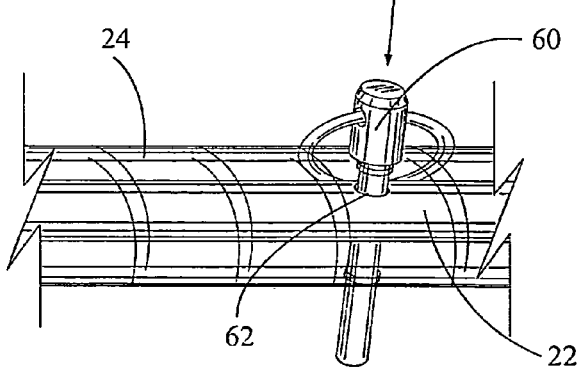
FIG. 2 illustrates a handle sleeve pinned to a torque bar.

In FIG. 2, a safety pin 60 is shown received through a hole 62 in the handle sleeve 24 and the torque bar 22. When the safety pin 60 is inserted, the handle sleeve 24 can now rotate the torque bar 22. It is important to note, the safety pin 60 is not inserted into the hole 62 until electrical power is applied to the computer 52 and the strain gauge 46 and prior to the proper programming of the computer for measuring the torque applied to the torque bar 22.

Figure 3:
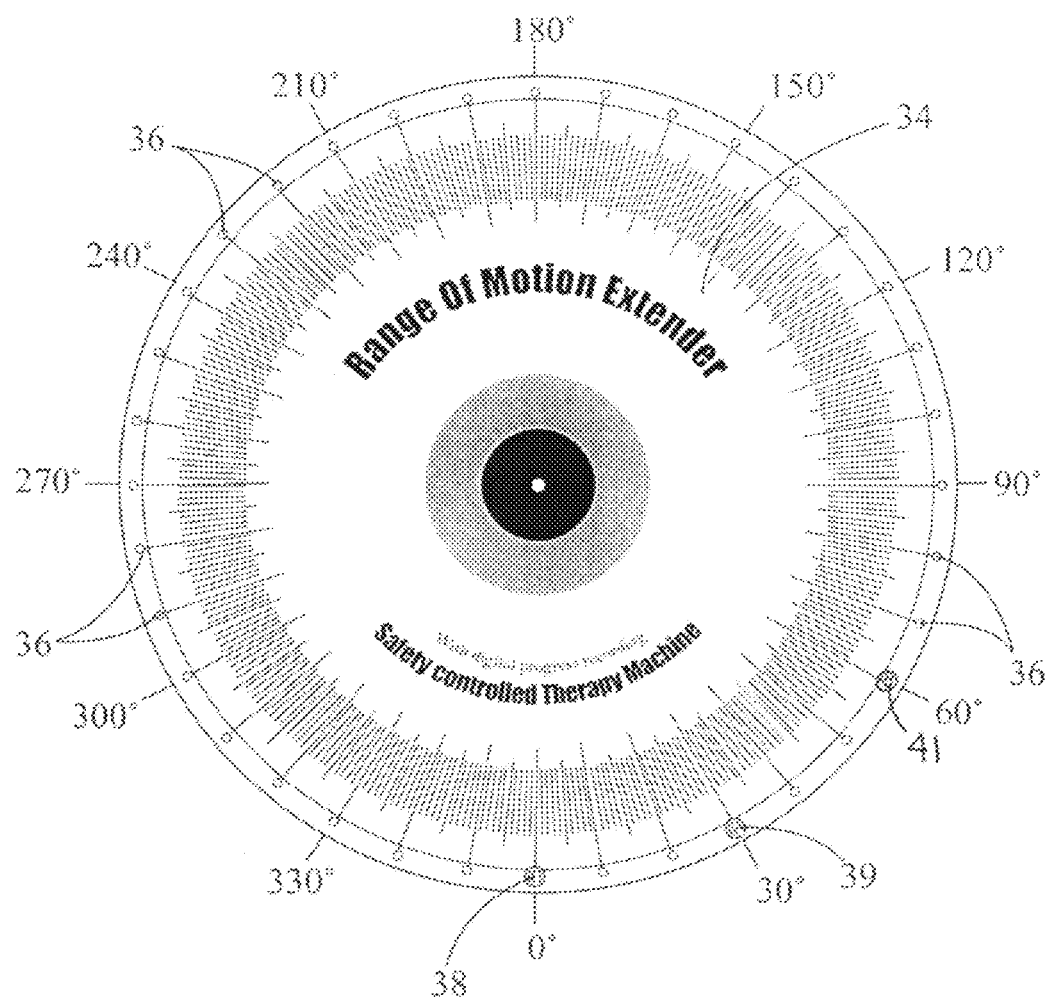
FIG. 3 is a front view of a range of motion scale used with the therapy evaluation machine.

In FIG. 3, a front view of the range of motion scale 34 is shown with measurements from zero to 360 degrees. In this drawing, the scale 34 is marked in 30 degree segments. Also shown in this drawing are the target pins 38 and 39 inserted into the target holes 36 at the zero and 30 degree positions. As a safety feature, a third target pin 41 is inserted, for example, at a 60 degree position on the scale 34. The third target pin 41 is used as a safety stop to prevent over-extending the torque on the strain gauge 46 and possibly damaging the gauge.

Figure 4:
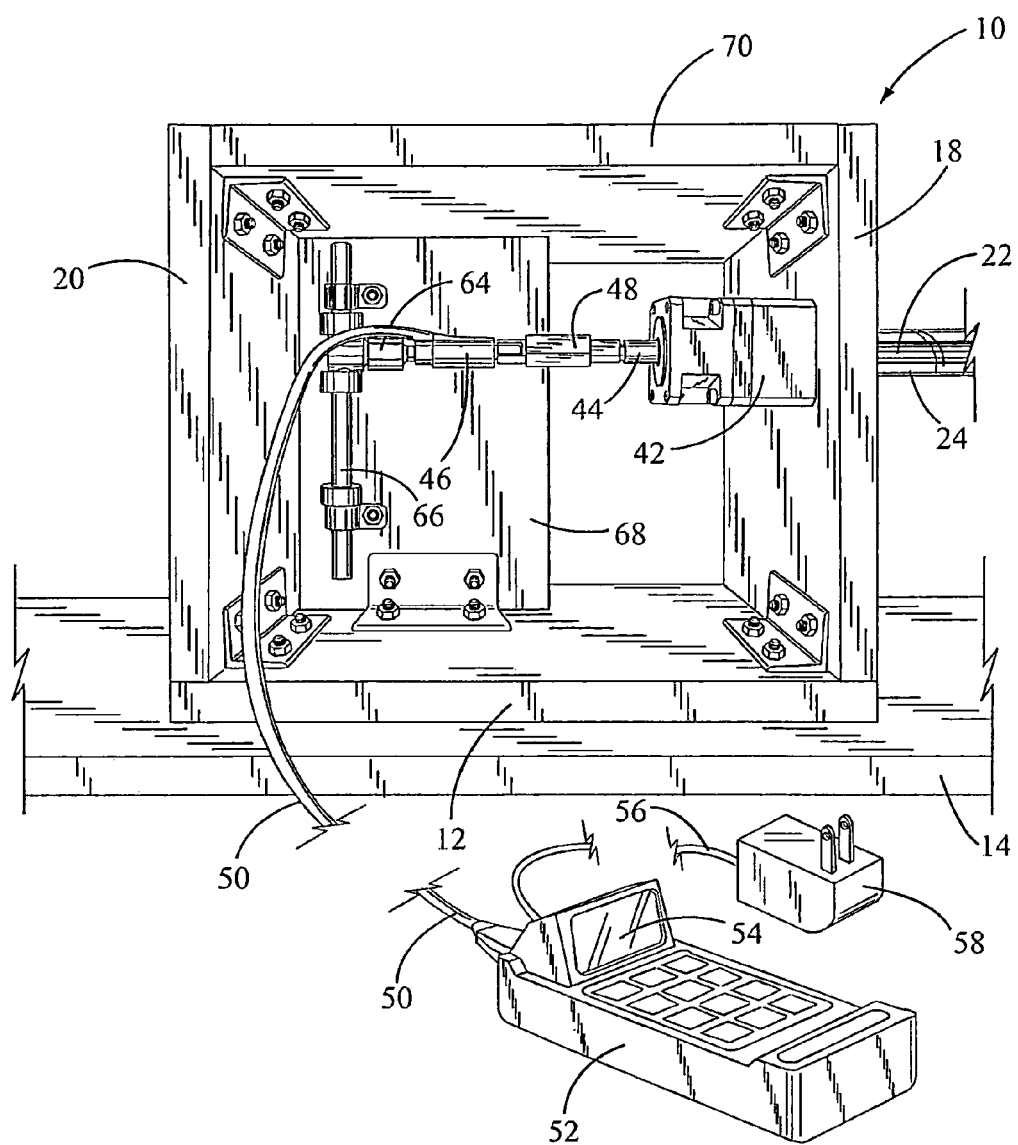
FIG. 4 is a front view of a portion of the therapy evaluation machine and illustrating a gear box and strain gauge used to develop and measure torque applied to the torque bar.

In FIG. 4, a front view of a portion of the therapy evaluation machine 10 is shown housing the gear box 42 and the strain gauge 46. In this drawing, the strain gauge 46 is attached to a fixed shaft 64 mounted to a vertical shaft 66. The vertical shaft 66 is attached to an upright panel 68, which is secured to the base 12 and a frame top 70.

In FIG. 5, the machine 10 is shown in operation with the hand 26 gripping the handle sleeve 24, which has been engaged with the torque bar 22, using the safety pin 60. As mentioned above and prior to this time, the computer 52 and the strain gauge 46 have been electrically powered up. The gear box 42 provides for increased torque ratios of both angular displacement and torque ranges associated to each respectively, for example from 3 to 1 or from 5 to 1, when coupled to the strain gauge 46. This feature provides for adjusting to male and female patients having different strengths in their wrists, hands and fingers. Also, the gear box 42 provides for rotating the torque bar 22 in either a clockwise or counterclockwise direction, as indicated by the two arrows 72.

In FIG. 6, the machine 10 is shown in operation with the fingers 32 gripping the finger grip 30 and rotating the torque bar 22 and the range of motion scale 34. For example, if the computer 52 has been programmed with the strain gauge 46 to measure 1.20 inch/pounds, as shown in FIG. 7, this would establish a linear curve 73 to measure a patient's progress of injury recovery over a 3 to 6 month period.

Figure 7:
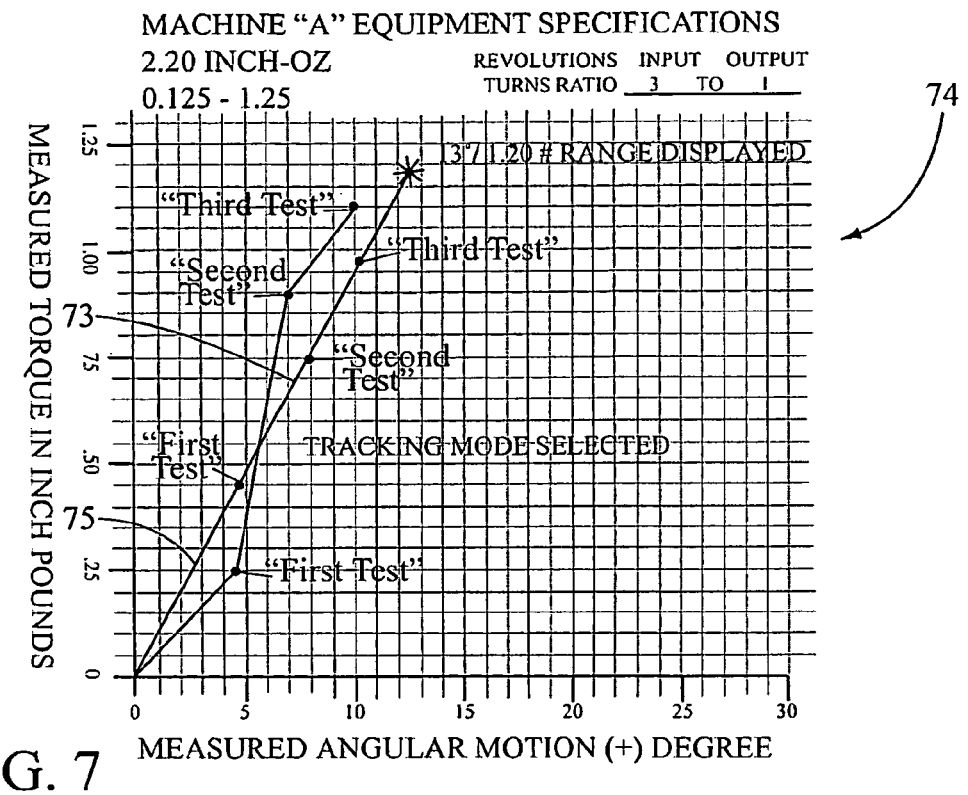
FIG. 7 is a progress report graph illustrating range of motion vs. measured torque in inch pounds. The graph shows three tests taken of an injured wrist, hand or fingers.

In FIG. 7, the computer 52 has been hooked up to a printer and a patient injury progress report graph, having general reference numeral 74, has been printed out for review by the patient and the physical therapist. In this example, the range of motion scale 34 has been used to measure angular motion in degrees of the injured wrist, hand or fingers. The strain gauge 46 has been used to originate and also to measure torque in inch pounds of the injured wrist, hand or fingers using the torque bar 22.

In this drawing, the gear box 42 has a gear ratio connected to the strain gauge 46 of 3 to 1. Through testing of adult males and as an example, it has been shown that the therapy evaluation machine 10 or machine "A" has a typical displacement of 13 degrees on the scale 34 and a torque of 1.20 inch pounds to establish the linear line 73. When a first male patient is first tested, the therapist confirms that the patient's healthy hand can displace the scale 34 with a torque of 1.20 inch pounds. When this patient is then tested with his injured hand, he can only displace the scale 5 degrees at 0.40 inch pounds. This test is marked "First Test" on the report graph 74. When the first patient returns for further testing or "Second Test" a month later, the injured wrist, hand or fingers now displace the scale 8 degrees at 0.75 inch pounds. Obviously, the patient's injury has improved. Further, when the patient returns again a month later for a "Third Test", the injured wrist, hand or fingers now displace the scale 12 degrees at 1.00 inch pounds. From reviewing the report graph 74, the machine 10 has helped the therapist confirm the male patient has made sufficient progress in injury recovery and has gained over 80% of the range of motion and torque of his injured wrist, hand or fingers when compared to his healthy wrist, hand or fingers.

As another example and using this drawing, a second male patient is first tested, the therapist confirms that the patient's healthy hand can displace the scale 34 with a torque of 1.20 inch pounds. When this patient is then tested with his injured hand, he can only displace the scale 5 degrees at 0.25 inch pounds. This test is marked "First Test" on a non-linear line 75. When the second patient returns for further testing or "Second Test" a month later, the injured wrist, hand or fingers now displace the scale 7 degrees at 0.9 inch pounds. Obviously, the patient's injury has improved. Further, when the second patient returns again a month later for a "Third Test", the injured wrist, hand or fingers now displace the scale 10 degrees at 1.10 inch pounds. From reviewing the report graph 75, the machine 10 has helped the therapist confirm the second male patient has made sufficient progress in injury recovery and has gained over 80% of the range of motion and torque of his injured wrist, hand or fingers when compared to his healthy wrist, hand or fingers.

Figure 8:
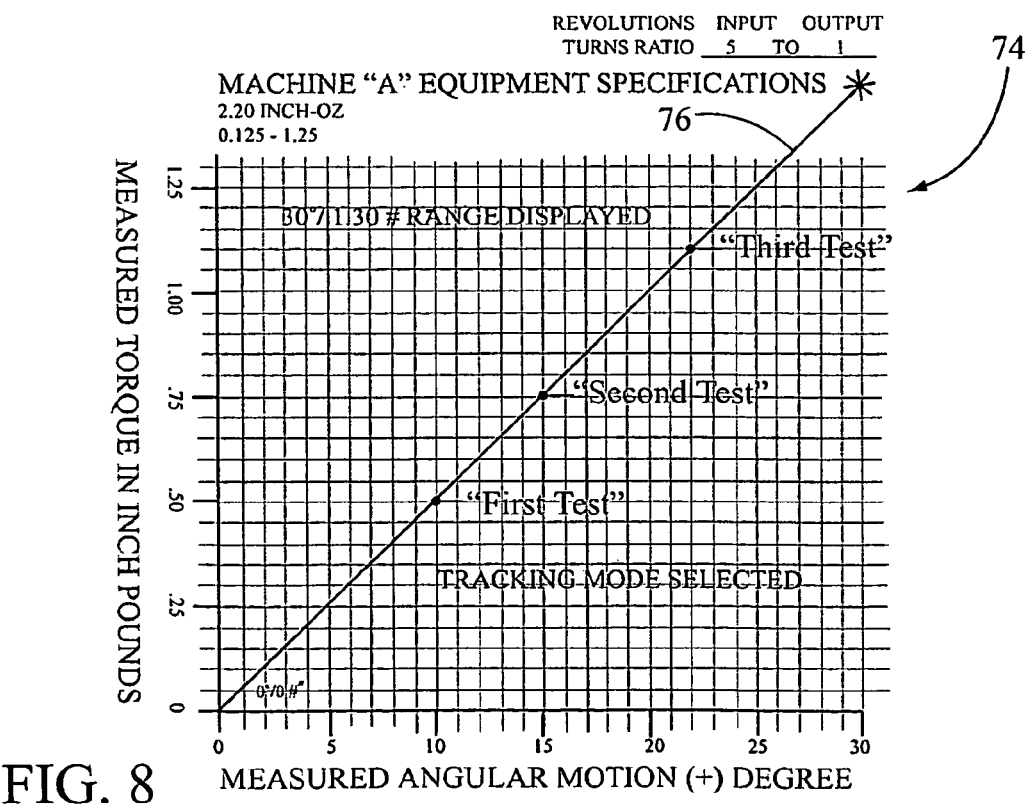
FIG. 8 is a similar report graph as shown in FIG. 7, but with a different gear ratio using the gear box mounted on the therapy evaluation machine.

In FIG. 8 is similar to FIG. 7 with the gear box 42 having gear ratio of 5 to 1. In this example, the progress report graph 74 has a linear line 76 with the therapy evaluation machine 10 or machine "A". The linear line 76 illustrates a typical displacement by a healthy hand or fingers of a male patient of 30 degrees on the scale and a torque of 1.30 inch pounds. When a third patient is first tested using this particular machine, the therapist confirms that the patient's healthy hand can displace the scale 30 degrees and with a torque of 1.30 inch pounds. When the third patient is then tested with his injured hand, he can only displace the scale 8 degrees at 0.40 inch pounds. This test is marked "First Test" on the report graph 74. When the patient returns for further testing or "Second Test" a month later, the injured wrist, hand or fingers now displaces the scale 15 degrees at 0.75 inch pounds. Obviously, the patient's injury has improved. Further, when the patient returns again a month later for a "Third Test", the injured wrist, hand or fingers now displace the scale 23 degrees at 1.10 inch pounds. From reviewing this report graph 74, the machine 10 has helped the therapist confirm the male patient has made sufficient progress in injury recovery and has gained over 70% of the range of motion and torque of his injured wrist, hand or fingers when compared to his healthy wrist, hand or fingers.

While the above therapy evaluation machine 10 has been discussed in providing a factual analysis of the recovery of an injury to the wrist, hand or fingers, the evaluation machine can be used equally in the measurement of injured joints in the arms and legs of a patient.

Also, while the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the subject invention for which an exclusive privilege and property right are claimed and defined as follows:

1. A therapy evaluation machine used for measuring range of motion during the rehabilitation of an injury to a patient's hand, the therapy evaluation machine comprising:
   a horizontal machine base, the base including an upwardly extending, vertical first frame member and a spaced apart, vertical second frame member;
   a horizontal exercise torque bar rotatably mounted on and suspended from the first and second frame members, the torque bar adapted for gripping and manual rotation by the patient's hand;
   a 360 degree, range of motion scale, the motion scale mounted on one end of the torque bar, the motion scale used for visually measuring range of motion in degrees by the manual rotation of the torque bar by the patient's hand;
   a gear box coupled to an opposite end of the torque bar, the gear box having increased torque ratios for measuring angular displacement and torque ranges when used by different strengths of the patient's hand; and
   a strain gauge coupled to the gear box, the strain gauge configured to be activated by the rotation of the torque bar, and the strain gauge configured to measure resistance to the torque bar during the manual rotation by the patient's hand.

2. The therapy evaluation machine as described in claim 1 further including a round finger grip, the finger grip attached to one end of the torque bar, the finger grip adapted for gripping and rotating the torque bar by at least two of the patient's fingers, the motion scale used for visually measuring range of motion in degrees by the fingers.

3. The therapy evaluation machine as described in claim 1 further including spaced apart target holes disposed around a circumference of the range of motion scale, the target holes for receiving a first target pin and a second target pin and an upwardly extending pointer attached to a top of a horizontal mounting plate, the first and second frame members received on the mounting plate, the first target pin disposed next to the pointer, the first target pin set at zero degrees on the motion scale, the second target pin is set at a selected degree on the scale for measuring the amount of range of motion by the patient's hand.

4. The therapy evaluation machine as described in claim 1 wherein the strain gauge is electrically connected to a computer with a digital display, the digital display used for monitoring the torque applied to the torque bar and the strain gauge, the computer connected to an electrical power outlet for providing power to the computer and the strain gauge.

5. A therapy evaluation machine used for measuring range of motion during the rehabilitation of an injury to a patient's hand or fingers, the therapy evaluation machine comprising:
   a horizontal machine base, the base including an upwardly extending, vertical first frame member and a spaced apart, vertical second frame member;
   a horizontal exercise torque bar rotatably mounted on and suspended from the first and second frame members, the torque bar adapted for gripping and manual rotation by the patient's hand;
   a 360 degree, range of motion scale, the motion scale mounted on the torque bar, the motion scale used for visually measuring range of motion in degrees by the manual rotation of the torque bar by the patient's hand;
   a gear box coupled to an opposite end of the torque bar, the gear box having increased torque ratios for angular displacement and torque ranges when used by different strengths of the patient's hand;
   a strain gauge coupled to the gear box, the strain gauge configured to be activated by the rotation of the torque bar, and the strain gauge configured to measure resistance to the torque bar during the manual rotation by the patient's hand; and
   a round finger grip, the finger grip attached to one end of the torque bar, the finger grip adapted for gripping and rotating the torque bar by at least two of the patient's fingers, the motion scale used for visually measuring range of motion in degrees by the fingers.

6. The therapy evaluation machine as described in claim 5 further including spaced apart target holes disposed around a circumference of the range of motion scale, the target holes for receiving a first target pin and a second target pin; and an upwardly extending pointer attached to a top of a horizontal mounting plate, the first and second frame members received on the mounting plate, the first target pin disposed next to the pointer, the first target pin is set at zero degrees on the motion scale, the second target pin is set at a selected degree on the scale for measuring the amount of range of motion by the patient's hand or fingers.

7. The therapy evaluation machine as described in claim 5 wherein the strain gauge is electrically connected to a computer with a digital display, the digital display used for monitoring the torque applied to the torque bar and the strain gauge, the computer connected to an electrical power outlet for providing power to the computer and the strain gauge.

8. A therapy evaluation machine used for measuring range of motion during the rehabilitation of an injury to a patient's hand or fingers, the therapy evaluation machine comprising:
   a horizontal machine base, the base including an upwardly extending, vertical first frame member and a spaced apart, vertical second frame member;
   a horizontal exercise torque bar rotatably mounted on and suspended from the first and second frame members, the torque bar adapted for gripping and manual rotation by the patient's hand;
   a round finger grip, the finger grip attached to one end of the torque bar, the finger grip adapted for gripping and rotating the torque bar by a least two of the patient's fingers;
   a 360 degree, range of motion scale, the motion scale mounted on the torque bar, the motion scale used for visually measuring range of motion in degrees by the manual rotation of the torque bar by the patient's hand or fingers;
   a gear box coupled to an opposite end of the torque bar, the gear box having increased torque ratios for angular displacement and torque ranges when used by different strengths of the patient's hand or fingers;
   a strain gauge coupled to the gear box, the strain gauge configured to be activated by the rotation of the torque bar, and the strain gauge configured to measure resistance to the torque bar during the manual rotation by the patient's hand; and a computer with a digital display connected to the strain gauge, the digital display used for monitoring the torque applied to the torque bar and the strain gauge, the computer connected to an electrical power outlet for providing power to the computer and the strain gauge.

9. The therapy evaluation machine as described in claim 8 further including spaced apart target holes disposed around a circumference of the range of motion scale, the target holes for receiving a first target pin and a second target pin; and an upwardly extending pointer attached to a top of a mounting plate, the first and second frame members received on the mounting plate, the first target pin disposed next to the pointer, whereby when the first target pin is set at zero degrees on the motion scale, the second target pin is set at a selected degree on the scale for measuring the amount of range of motion by the patient's hand or fingers.

\* \* \* \* \*